United States Patent
Quereshi et al.

(10) Patent No.: US 6,375,769 B1
(45) Date of Patent: Apr. 23, 2002

(54) METHOD OF APPLYING CURVED LEG ELASTICS USING PUCKS WITH CURVED SURFACES

(75) Inventors: Shawn A. Quereshi; Joseph D. Coenen; Robert Eugene Vogt, all of Neenah; Robert Lee Popp, Hortonville; Donald J. Sanders, Larsen, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 66 days.

(21) Appl. No.: 09/642,208

(22) Filed: Aug. 15, 2000

(51) Int. Cl.$^7$ ............................................. B32B 31/16
(52) U.S. Cl. ...................... 156/73.1; 156/161; 156/229; 156/256; 156/290
(58) Field of Search ................................. 156/73.1, 160, 156/161, 164, 229, 250, 256, 264, 290

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,371,668 A | 3/1968 | Johnson | 128/290 |
| 3,468,748 A | 9/1969 | Bassett | 161/122 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,061,063 A | 12/1977 | Brush | 83/55 |
| 4,300,562 A | 11/1981 | Pieniak | 128/287 |
| 4,300,967 A | 11/1981 | Sigl | 156/164 |
| 4,340,563 A | 7/1982 | Appel et al. | 264/518 |
| 4,371,417 A | 2/1983 | Frisk et al. | 156/495 |
| 4,397,704 A | 8/1983 | Frisk | 156/201 |
| 4,412,881 A | 11/1983 | Sigl | 156/164 |
| 4,432,823 A | 2/1984 | Moore | 156/164 |
| 4,486,192 A | 12/1984 | Sigl | 604/385 |
| 4,578,133 A | 3/1986 | Oshefsky et al. | 156/164 |
| 4,610,681 A | 9/1986 | Strohbeen et al. | 604/395 |
| 4,617,082 A | 10/1986 | Oshefsky et al. | 156/447 |
| 4,639,949 A | 2/1987 | Ales et al. | 2/400 |
| 4,641,381 A | 2/1987 | Heran et al. | 2/400 |
| 4,642,819 A | 2/1987 | Ales et al. | 2/400 |
| 4,646,362 A | 3/1987 | Heran et al. | 2/400 |
| 4,648,928 A | 3/1987 | Ales | 156/164 |

(List continued on next page.)

FOREIGN PATENT DOCUMENTS

| | | | | |
|---|---|---|---|---|
| CA | 1338133 | 3/1996 | | 117/26 |
| EP | 0 217 032 | 4/1987 | | D04H/13/00 |

Primary Examiner—James Sells
(74) Attorney, Agent, or Firm—Pauley Petersen Kinne & Erickson

(57) ABSTRACT

A method of applying curved leg elastics to absorbent garments involves stretching and wrapping a pair of elastic ribbons about a first curved surface of a pair of pucks. A portion of each of the elastic ribbons is simultaneously folded onto a second surface of each of the pucks. The pucks are attached to a rotating device that rotates the pucks into alignment with a substrate. As the pucks are rotated toward the substrate, the pucks are also oscillated individually toward the substrate. Once the second surfaces of the pucks are aligned parallel to the substrate, the substrate is bonded to the second surface portion of each of the elastic ribbons in their stretched positions on the pucks, thereby forming finished seams. The resulting absorbent garments have gasket-like leg openings with improved comfort and aesthetic appeal.

29 Claims, 8 Drawing Sheets

U.S. PATENT DOCUMENTS

| | | | |
|---|---|---|---|
| 4,650,532 A | 3/1987 | Kloehn et al. | 156/204 |
| 4,663,220 A | 5/1987 | Wisneski et al. | 428/221 |
| 4,675,016 A | 6/1987 | Meuli et al. | 604/385 A |
| 4,687,477 A | 8/1987 | Suzuki et al. | 604/385 A |
| 4,726,873 A | 2/1988 | Ales et al. | 156/495 |
| 4,743,241 A | 5/1988 | Igaue et al. | 604/385 A |
| 4,747,846 A | 5/1988 | Boland et al. | 604/38 A |
| 4,786,346 A | 11/1988 | Ales et al. | 156/160 |
| 4,863,542 A | 9/1989 | Oshefsky et al. | 156/160 |
| 4,915,767 A | 4/1990 | Rajala et al. | 156/440 |
| 4,917,746 A | 4/1990 | Kons et al. | 156/164 |
| 4,940,464 A | 7/1990 | Van Gompel et al. | 604/396 |
| 4,943,340 A | 7/1990 | Ujimoto et al. | 156/496 |
| 4,946,539 A | 8/1990 | Ales et al. | 156/495 |
| 5,046,272 A | 9/1991 | Vogt et al. | 38/143 |
| 5,055,103 A | 10/1991 | Nomura et al. | 604/385.2 |
| 5,092,861 A | 3/1992 | Nomura et al. | 604/385.2 |
| 5,104,116 A | 4/1992 | Pohjola | 271/185 |
| 5,143,679 A | 9/1992 | Weber et al. | 264/288.8 |
| 5,147,487 A | 9/1992 | Nomura et al. | 156/164 |
| 5,156,793 A | 10/1992 | Buell et al. | 264/288.8 |
| 5,167,897 A | 12/1992 | Weber et al. | 264/288.8 |
| 5,171,388 A | 12/1992 | Hoffman et al. | 156/164 |
| 5,180,534 A | 1/1993 | Thomas et al. | 264/145 |
| 5,213,645 A | 5/1993 | Nomura et al. | 156/164 |
| 5,224,405 A | 7/1993 | Pohjola | 83/24 |
| 5,226,992 A | 7/1993 | Morman | 156/62.4 |
| 5,230,851 A | 7/1993 | Thomas | 264/145 |
| 5,259,902 A | 11/1993 | Mckenfuhs | 156/164 |
| 5,275,676 A | 1/1994 | Rooyakkers et al. | 156/164 |
| 5,318,741 A | 6/1994 | Thomas | 264/519 |
| 5,326,415 A | 7/1994 | Thomas et al. | 156/244.11 |
| 5,334,152 A | 8/1994 | Nomura et al. | 604/385.2 |
| 5,342,341 A | 8/1994 | Igaue et al. | 604/385.2 |
| 5,354,400 A | 10/1994 | Lavash et al. | 156/227 |
| 5,385,706 A | 1/1995 | Thomas | 264/519 |
| 5,389,173 A | 2/1995 | Merkatoris et al. | 156/164 |
| 5,393,360 A | 2/1995 | Bridges et al. | 156/73.3 |
| 5,407,507 A | 4/1995 | Ball | 156/163 |
| 5,413,654 A | 5/1995 | Igaue et al. | 156/161 |
| 5,454,803 A | 10/1995 | Sageser et al. | 604/385.2 |
| 5,500,075 A | 3/1996 | Herrmann | 156/494 |
| 5,503,919 A | 4/1996 | Litchholt et al. | 428/286 |
| 5,509,985 A | 4/1996 | Kock | 156/160 |
| 5,516,392 A | 5/1996 | Bridges et al. | 156/160 |
| 5,517,737 A | 5/1996 | Viltro et al. | 26/88 |
| 5,518,566 A | 5/1996 | Bridges et al. | 156/161 |
| 5,525,175 A | 6/1996 | Blenke et al. | 156/161 |
| 5,540,672 A | 7/1996 | Roessler et al. | 604/385.2 |
| 5,547,531 A | 8/1996 | Allen et al. | 156/164 |
| 5,556,504 A | 9/1996 | Rajala et al. | 156/519 |
| 5,622,578 A | 4/1997 | Thomas | 156/66 |
| 5,662,636 A | 9/1997 | Benjamin et al. | 604/385.2 |
| 5,704,930 A | 1/1998 | Lavash et al. | 604/385.2 |
| 5,716,478 A | 2/1998 | Boothe et al. | 156/302 |
| 5,723,087 A | 3/1998 | Chappell et al. | 264/284 |
| 5,733,401 A | 3/1998 | Linman et al. | 156/160 |
| 5,745,922 A | 5/1998 | Rajala et al. | 2/243.1 |
| 5,749,865 A | 5/1998 | Yamamoto et al. | 604/385.2 |
| 5,749,989 A | 5/1998 | Linman et al. | 156/160 |
| 5,759,340 A | 6/1998 | Boothe et al. | 156/519 |
| 5,772,825 A | 6/1998 | Schmitz | 156/164 |
| 5,776,121 A | 7/1998 | Roe et al. | 604/385.1 |
| 6,287,409 B1 * | 9/2001 | Stephany | 156/164 |

* cited by examiner

METHOD OF APPLYING CURVED LEG ELASTICS USING PUCKS WITH CURVED SURFACES

FIELD OF THE INVENTION

This invention is directed to a method of producing fully encircling, curved leg elastics. The method involves placing a pair of elastic ribbons on a pair of semi-curved pucks, each puck having a curved surface adjacent a preferably curved top surface, and subsequently applying the elastic ribbons to a substrate.

BACKGROUND OF THE INVENTION

Pant-like absorbent garments, such as adult incontinence wear, as well as infant and children's diapers, swim wear and training pants, typically include a pair of leg openings having an elastic portion around each leg opening. The elastic portions are intended to fit snugly around a wearer's legs to prevent leakage from the garment.

Various technologies are known for applying leg elastics to such articles. For example, one technology involves bonding a continuous loop to a substrate. However, producing a supply of continuous loops of elastic strands is more costly and cumbersome than providing a supply of a continuous length of elastic ribbons.

Articles which incorporate conventional elasticized margins and conventional barrier flap configurations at their leg openings have, however, exhibited various shortcomings. For example, it has been difficult to avoid pressure-induced marking of the wearer's skin and difficult to maintain the desired gasketing of the leg openings when the articles are being worn. Even when the leg openings are fitted with an elastomeric material or otherwise elasticized, it has been difficult to maintain contact between the leg opening and the wearer's body for an effective containment of urine and feces. As a result, there has been a continued need for improved containment structures at the leg regions of the absorbent articles.

There is a need or desire for a process for making comfortable, gasket-like leg elastics that are aesthetically pleasing and can be applied in a high-speed application.

SUMMARY OF THE INVENTION

The present invention is directed to a method of applying curved leg elastics to pant-like absorbent garments using semi-curved pucks. The result is a comfortable, flexible, aesthetically pleasing leg opening. Furthermore, the resulting leg opening is form-fitting and acts like a gasket.

Apparatus that can be used for carrying out the invention includes a pair of rotating devices, with at least one corresponding semi-curved puck attached to a periphery of each of the rotating devices. Each puck has a first curved surface adjacent a preferably curved second surface. The apparatus also includes a pair of cutting devices and a pair of bonding devices.

In carrying out the invention, each elastic ribbon of a pair of elastic ribbons is guided onto one of the pucks on one of the rotating devices, deflected to conform to the first curved surface of the puck, and cut off with a cutting device after conforming to a length of the first curved surface of the puck. The elastic ribbons are guided onto the pucks such that a portion of each of the elastic ribbons overhangs the edge of the first curved surface of the corresponding puck. Tension in the elastic ribbon causes the overhanging portion to fold over onto the adjacent second surface of the puck around which the elastic ribbon is stretched. Alternatively, the elastic ribbons may already be in discrete lengths prior to carrying out the method of the invention. A vacuum and/or friction surface is used to hold the elastic ribbons in place on the pucks. The rotating devices continue to advance the pucks toward the bonding devices. While the rotating devices rotate, the pucks are radially displaced from a position at which the elastic ribbons are guided onto the pucks to a position wherein the second surfaces of the pucks are substantially parallel to a substrate. Once the pucks are substantially parallel to and in contact with the substrate, the portions of the elastic ribbons folded onto the second surfaces of the pucks are bonded to the substrate. The substrate is typically a liner or an outer cover of the absorbent garment.

The method of the invention can be used in high-speed applications, namely applications running at linear speeds of 600 feet per minute or greater. More than one corresponding pair of semi-curved pucks can be located on the peripheries of the rotating devices to enable a more expedient process. The rotating devices can be adjusted to change pitch or machine direction spacing between adjacent pucks from the point of application of the elastic ribbons to the pucks to the point where the elastic ribbons are transferred and bonded to the substrate.

The substrate may be stretchable or extensible, thereby providing great flexibility and enabling the elastic ribbons to be applied at low tension. Furthermore, stretchability and/or extensibility of the substrate provide for a larger leg fit range.

The resulting product is an absorbent garment having a comfortable, aesthetically pleasing, finished look about the leg openings. This method can also be used to apply curved standing leg cuffs and/or curved leak guard flaps.

With the foregoing in mind, it is a feature and advantage of the invention to provide a method of applying curved leg elastics to an absorbent garment.

It is another feature and advantage of the invention to provide a method of applying leg elastics to an absorbent garment resulting in gasket-like leg openings.

It is yet another feature and advantage of the invention to provide a method of applying leg elastics to an absorbent garment resulting in form-fitting leg openings.

It is a further feature and advantage of the invention to provide a method of applying leg elastics to an absorbent garment resulting in comfortable and aesthetically pleasing leg openings.

DEFINITIONS

Figure 1:
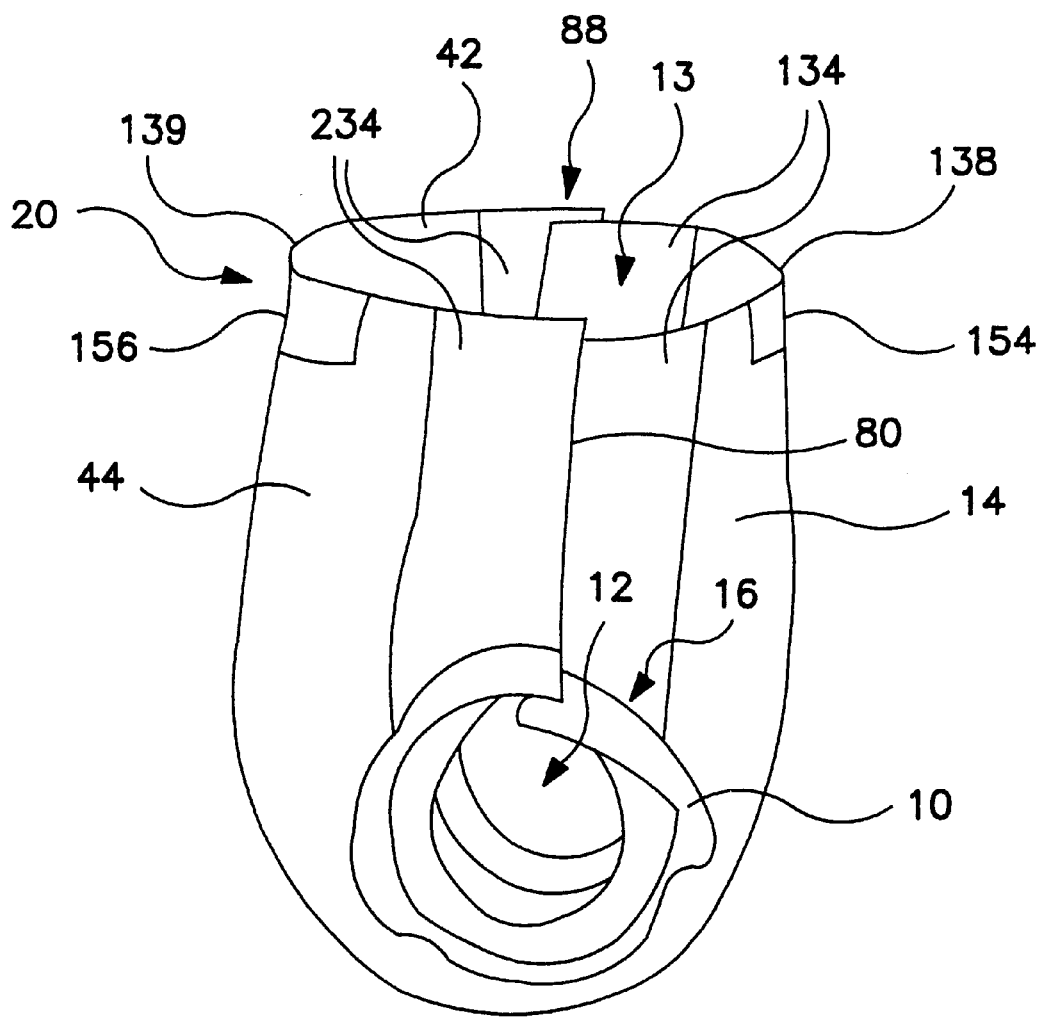
FIG. 1 is a side perspective view of an absorbent garment.

Within the context of this specification, each term or phrase below will include the following meaning or meanings. "Bonded" refers to the joining, adhering, connecting, attaching, or the like, of two elements. Two elements will be considered to be bonded together when they are bonded directly to one another or indirectly to one another, such as when each is directly bonded to intermediate elements. "Curved" refers to an opening, band, flap, surface, or edge, at least a portion of which is curved, i.e. has a radius of curvature and an arc covering at least 30°. Preferably, the opening, band, flap, surface, or edge is curved over at least 90°, more preferably at least 180°.

"Disposable" refers to articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to a material capable of being extended or protruded in length or breadth.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid. The term also includes film-like materials that exist as open-celled foams.

"Force" includes a physical influence exerted by one body on another which produces acceleration of bodies that are free to move and deformation of bodies that are not free to move.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Leg elastic" includes elastic bands, strands, ribbons, filaments, filament bunches and the like, which are adjacent to a garment opening that receives a wearer's leg.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid-permeable material" or "liquid water-permeable material" refers to a material present in one or more layers, such as a film, nonwoven fabric, or open-celled foam,. which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 10:
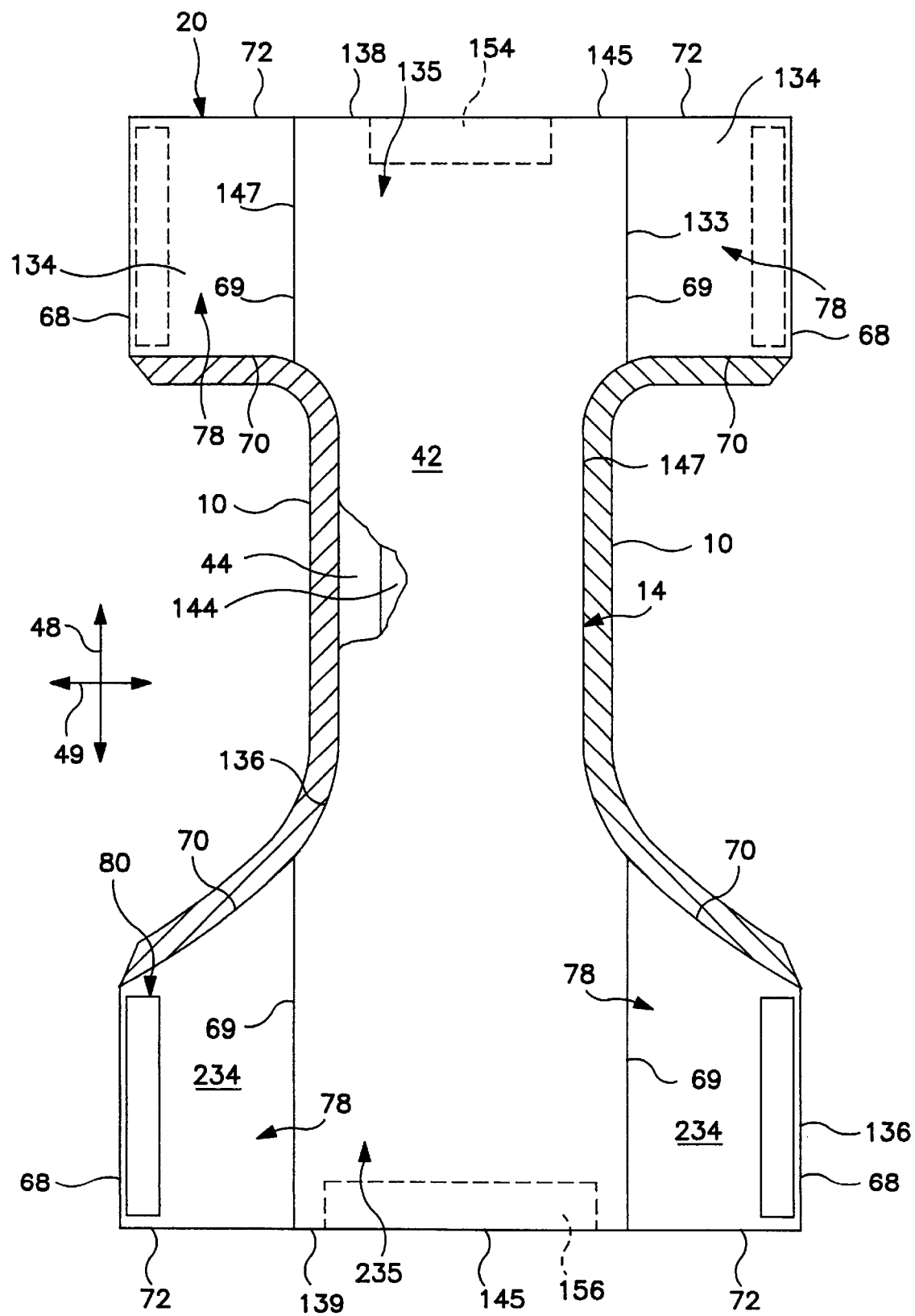
FIG. 10 is a plan view of the absorbent garment of FIG. 1 in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes depicted in FIG. 10. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively attached," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the composite. The joining, attaching, connecting or the like can be either directly, such as joining either member directly to an element, or can be indirectly by means of another member disposed between the first member and the first element, or can be such that a first member is mechanically trapped by adjacent bond points in a first element such that the first member causes the composite to exhibit characteristics of the first member.

"Polymers" include, but are not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a method of applying curved leg elastics to pant-like absorbent garments. Curved leg elastics, in accordance with the invention, are leg elastics that follow a curved contour of a leg opening. The present invention results in curved leg elastics having an unbonded elastic portion spanning an entire length of the leg elastics and a bonded elastic portion also spanning an entire length of the leg elastics. The unbonded portion and the bonded portion are both part of a solitar unit, or ribbon, of elastic. The bonded portion is a portion of the elastic ribbon that is bonded to a substrate. The unbonded portion can extend away from the bonded portion at an angle, or can lie juxtaposed to the bonded portion via a fold along the length of the elastic ribbon. The unbonded portion has greater freedom to respond to internal tension when the garment is in a relaxed state than the bonded portion, attributable to the fact that the bonded portion is bonded to the substrate in a stretched state, thereby causing the bonded portion to be restrained in movement by the substrate. The resulting disproportionate freedom of movement along the length of the elastic ribbon causes a curvature of the elastic ribbon. In addition to the curvature caused by the disproportionate freedom of movement, the bonded portion is bonded to the substrate along a periphery of a curved cut-out in the substrate. The curved shape of the bonded portion increases the curvature of the leg elastics.

The principles of the present invention can be incorporated into any suitable disposable absorbent article. Examples of such suitable articles include diapers, training pants, feminine hygiene products, incontinence products, other personal care or health care garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant. Furthermore, the principles of the present invention can be used to apply leg elastics, crotch elastics, as well as leak guard flaps or leg cuffs, to the leg openings of pant-like absorbent garments. For ease of explanation, the description hereafter will be in terms of leg elastics.

Referring to FIG. 1, a disposable absorbent article, such as a training pant 20, is illustrated in a fastened condition. Leg elastics 10 are used around leg openings 12 of the training pant 20 to create a gasket and to reduce or prevent leakage. The term "gasket" refers to a device that is used to block fluid leakage around the leg openings, between the garment and legs of a wearer. A main chassis 14 defines the leg openings 12 and a waist opening 13. When the leg elastics 10 are curved, as in the present invention, the leg elastics 10 are more form-fitting than straight edge leg elastics. The term "straight edge leg elastics" refers to typical leg elastics that are attached to a substrate in a straight line. With curved leg elastics, the leg openings 12 are gathered with low tension, since the leg openings 12 do not have to overcome forces from a main chassis 14 as straight edge leg elastics must overcome. The low tension and form-fit results in an absorbent garment 20 with increased comfort. Additionally, the curved leg elastics 10 have a finished seam 16 where attached to the main chassis 14, resulting in an aesthetically pleasing appearance.

Figure 2:
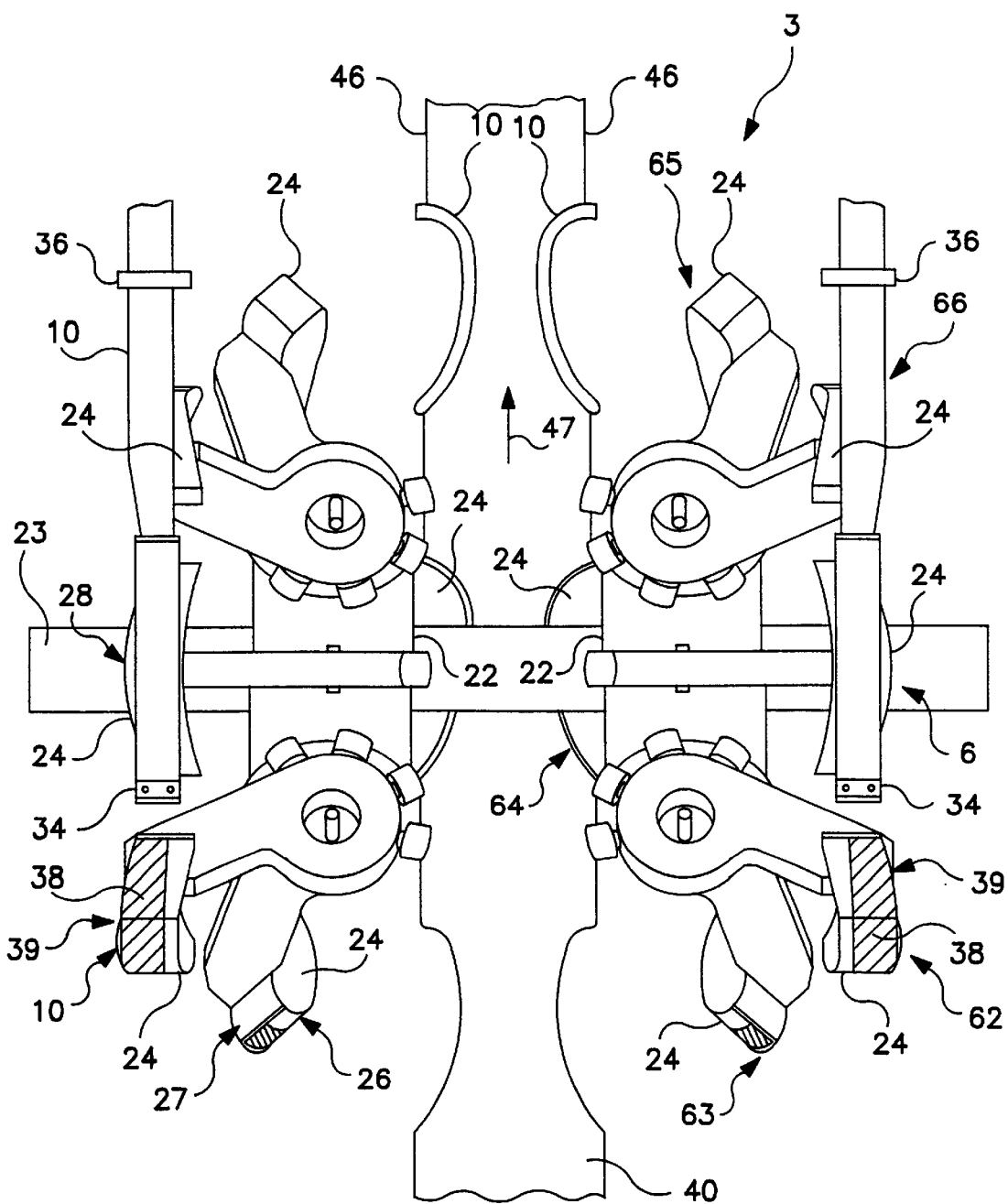
FIG. 2 is a top view of apparatus, including two rotating devices each having six pucks, used to produce curved leg elastics.
Figure 3:
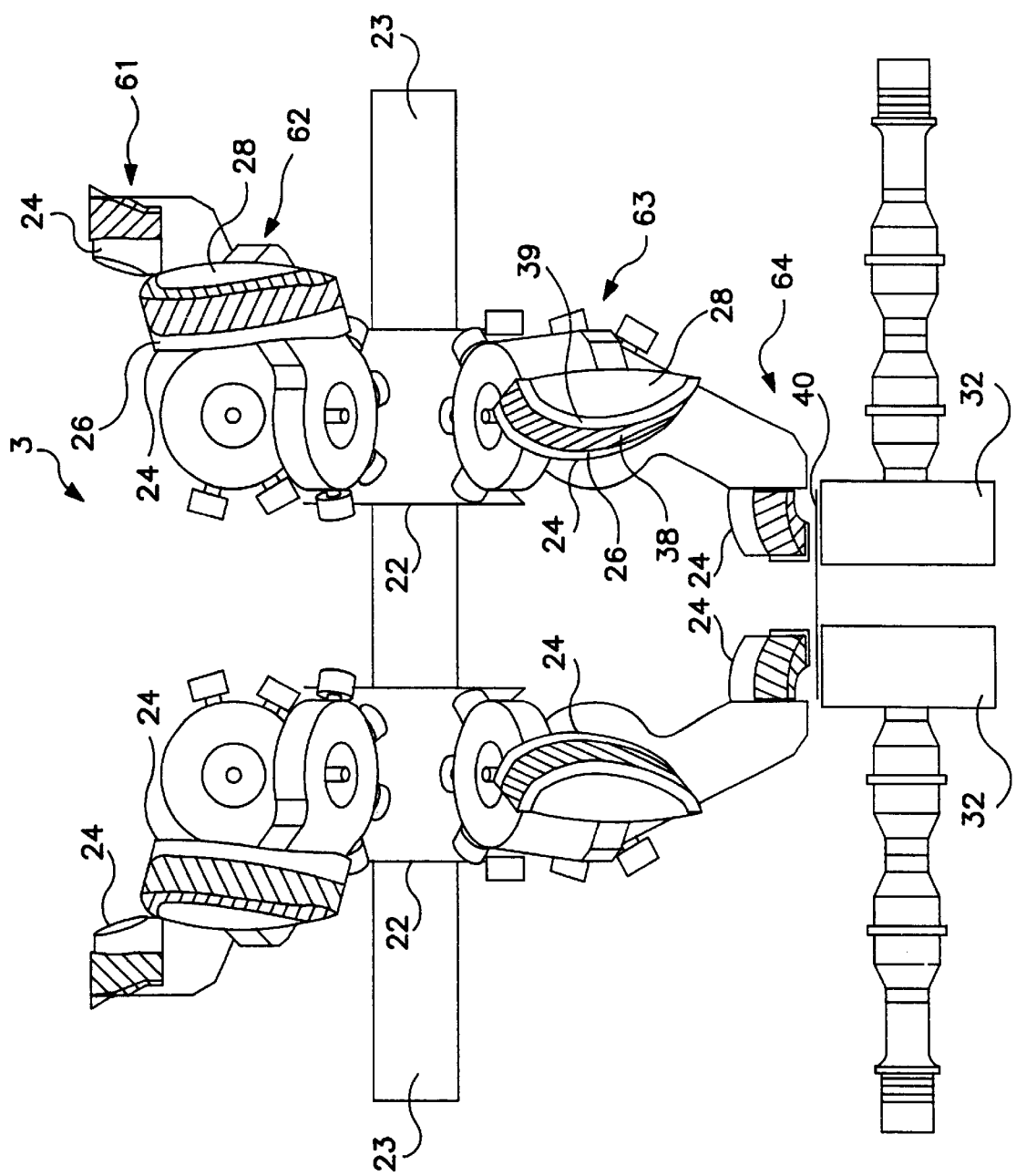
FIG. 3 is a front view of the apparatus in FIG. 2, showing four of the pucks on each of the rotating devices.
Figure 4:
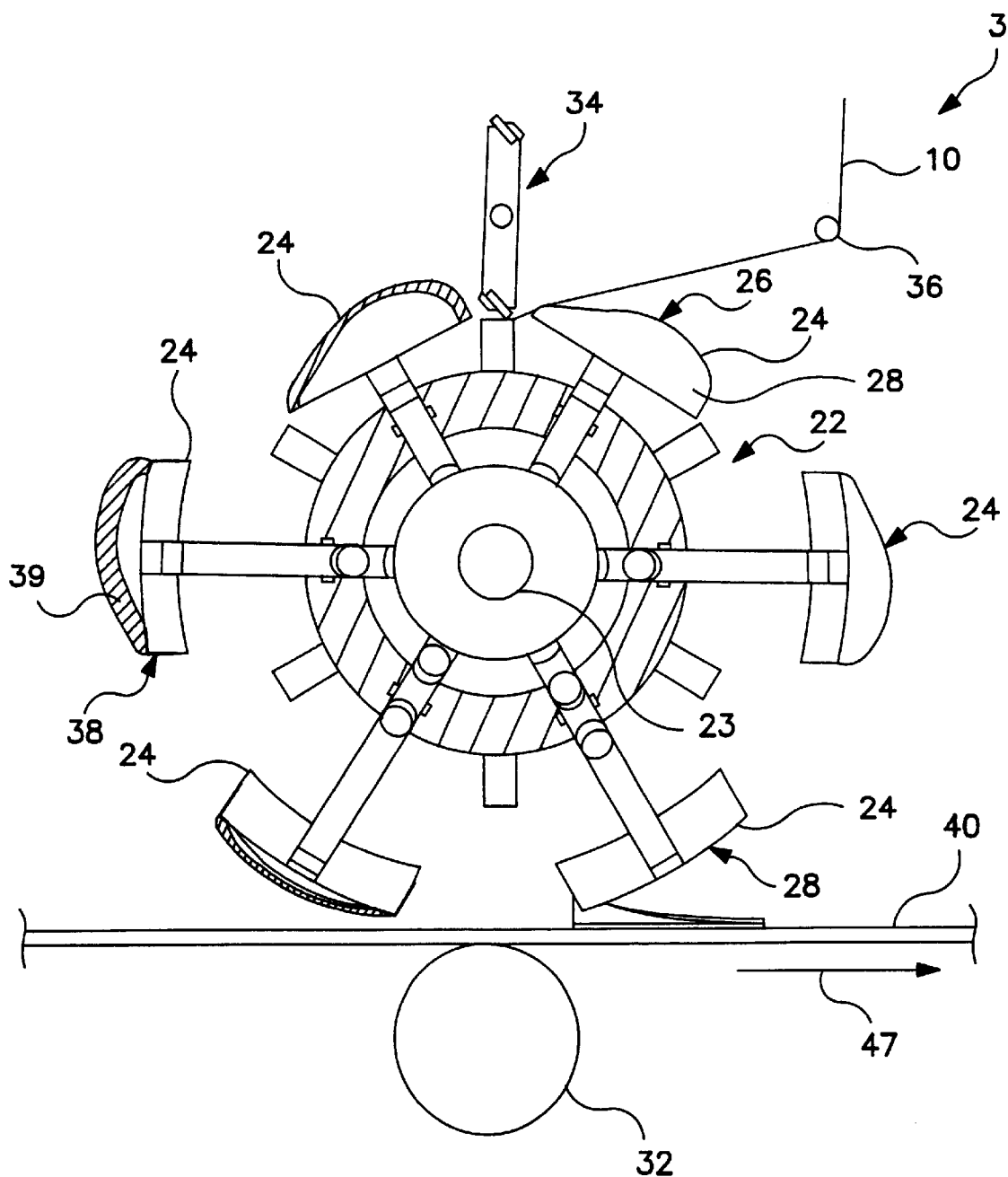
FIG. 4 is a side view of the apparatus of FIGS. 2 and 3, showing six of the pucks in six different positions.

One example of apparatus 3 for carrying out the invention is shown generally in FIGS. 2, 3 and 4. The apparatus 3 includes a pair of rotating devices 22 with at least one pair of corresponding semi-curved pucks 24 attached to a periphery of the corresponding rotating devices 22. Six pairs of semi-curved pucks 24 are shown in FIG. 2. Four pairs of pucks are shown in FIG. 3. The other two pairs of pucks are not shown in FIG. 3 for reasons of clarity. The term "semi-curved" refers to a puck having at least one curved surface which extends partially around the puck, but less than all the way around the puck. The semi-curved pucks 24 of the present invention preferably have curved contours on at least two adjacent surfaces. The curved surfaces may vary in terms of degrees of curvature along their lengths, with optimal curvature of a first surface 26 conforming to curvature about a wearer's leg, and optimal curvature of a second surface 28 such that the second surface 28 forms a rolling action when the puck 24 is in position to transfer and bond an elastic ribbon 10 to a substrate 40. Preferably, the first curved surface 26 extends about 90–270° around the puck, more preferably about 135–225°. Similarly, the leg elastics 10 are preferably curved about the full circumference of the leg openings 12, but may alternatively only partially encircle the leg openings 12, thereby resulting in curved leg elastics that are not fully encircling.

Figure 5:
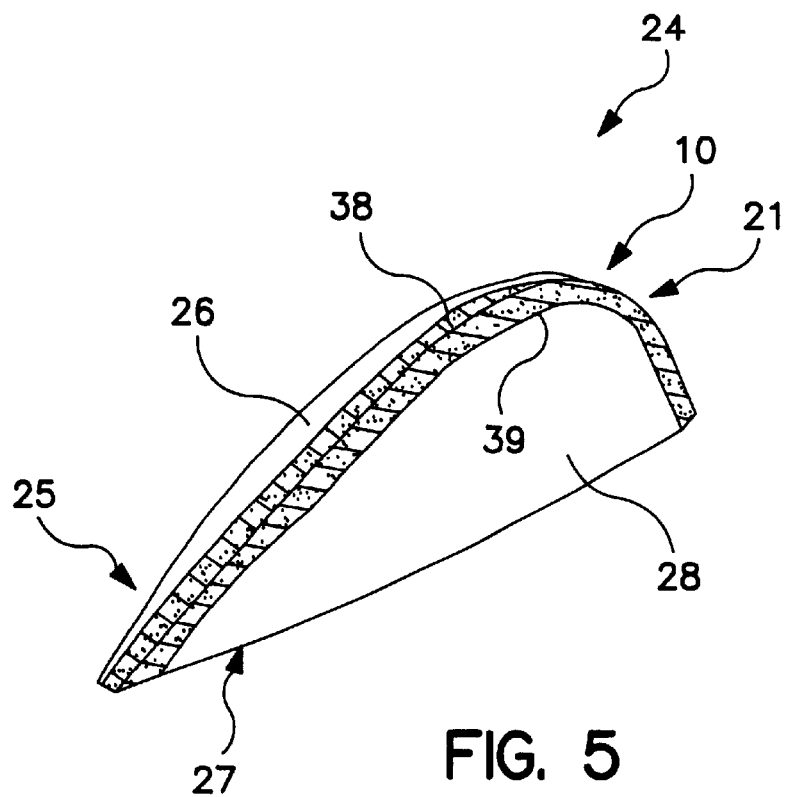
FIG. 5 is a perspective view of one of the pucks of the apparatus shown in FIGS. 3 and 4, wherein the puck is in a position prior to a bonding position.
Figure 6:
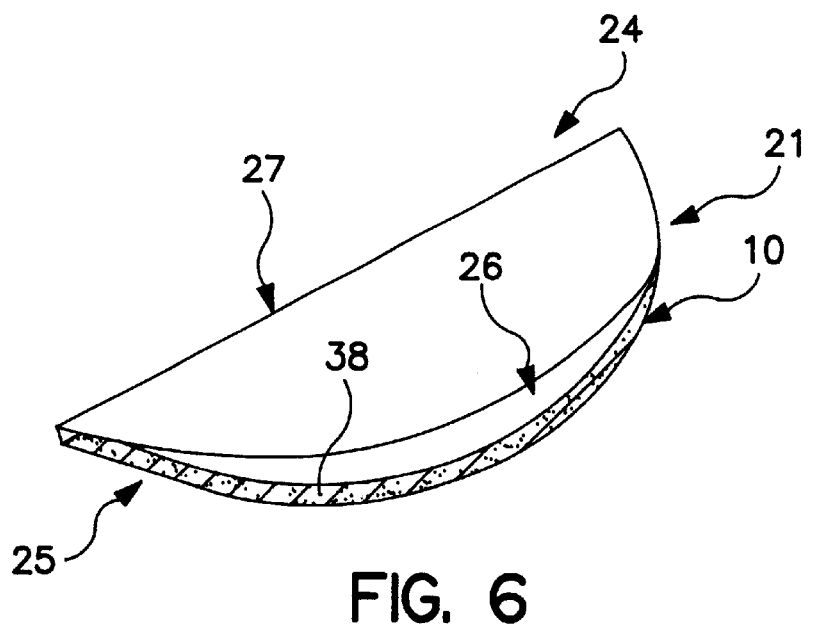
FIG. 6 is a perspective view of the puck in FIG. 5, wherein the puck has been rotated to be placed in a suitable bonding position.

A semi-curved puck 24 used in the invention is shown separately in FIGS. 5 and 6. As mentioned above, the puck 24 has a first curved surface 26, a back wall 27, and a second surface 28, preferably having a curvature corresponding to the radius of the rotating device 22 (FIGS. 2–4). The first curved surface 26 is preferably curved more at one end 21 than at the other end 25, as shown in FIGS. 5 and 6. The puck can have a back wall 27 of any shape, including flat, as shown in FIGS. 5 and 6, curved or even a concave curvature following the shape of the first curved surface 26. FIGS. 5 and 6 also show a tensioned elastic ribbon 10 wrapped about the first curved surface 26 of the puck 24, as explained below.

The rotating devices 22 each rotate about an axis 23 in a direction complementary to the machine direction movement of the substrate 40. The machine direction is indicated by the arrow 47 in FIGS. 2 and 4. The machine direction in FIG. 3 is into the paper. Guide rolls 36 and a cutting device 34 are located in close proximity to each of the rotating devices 22, but not necessarily in close proximity to one another (FIG. 4). As shown in FIG. 4, the cutting devices 34 may also be used to deflect the web path of the elastic ribbons 10 onto the pucks 24. A bonding device 32, such as an ultrasonic bonder, is also located in close proximity to each of the rotating devices 22, and may be located below the substrate 40, as shown in FIGS. 3 and 4. The pucks 24 can either rotate onto the substrate 40 with sufficient pressure for the bonding process or, alternatively, the bonding devices 32 can exert force upward to carry out the bonding process.

In carrying out the invention, as shown in FIG. 2, the elastic ribbons 10 are guided through the cutting devices 34 and onto the pucks 24 as the rotating devices 22 rotate. As the elastic ribbons 10 are guided through the cutting devices 34, the cutting devices are used to deflect the elastic ribbons 10 to follow the contours of the first curved surfaces 26 of the pucks 24. As the pucks 24 are rotated past the cutting devices 34, the cutting devices 34 displace the elastic ribbons 10 causing them to conform to the first curved surface 26 of the pucks 24 and subsequently cut the elastic ribbons 10 into discrete pieces or segments. Examples of suitable cutting devices 34 include mechanical pinch type cut-off knives, shear type cut-off knives, and hot knives or other cutting means well known in the art. A vacuum within the pucks 24 is used to hold the elastic ribbons 10 in place on the pucks 24. Alternatively or additionally, the pucks 24 can have a nonslip texture on at least part of the first curved surfaces 26 and on at least part of the adjacent second curved surfaces 28 to hold the elastic ribbons 10 in place. The elastic ribbons 10 are guided onto the first curved surfaces 26 of the pucks 24 such that a first portion 38 of the elastic ribbons 10 is placed on the first curved surfaces 26 of the pucks 24 while a second portion 39 of the elastic ribbons 10 overhangs the edge of the first curved surface 26. Tension in the elastic ribbons 10 and the curvature of the first surface 26 cause the second portion 39 of the elastic ribbons 10 to fold onto the adjacent second curved surfaces 28 of the pucks 24. The elastic ribbons 10 are preferably stretched to at least 125%, more preferably at least 150%, of their initial (unstretched) length as they are wrapped about the first curved surface 26 of the puck 24. The cutting device 34 is not necessarily directly mounted to the rotating device 22, but is mounted at least in close proximity to the rotating device 22.

Once the elastic ribbons 10 have been cut into discrete lengths, the pucks 24 are rotated (approximately 45–135 degrees) from the position shown in FIG. 5 to the position shown in FIG. 6. The puck 24 in FIG. 5 is in roughly the same orientation as the pucks 24 indicated by the arrow 61 in FIGS. 2 and 3. Similarly, the puck 24 in FIG. 6 is in roughly the same orientation as the pucks 24 indicated by the arrow 64 in FIGS. 2 and 3. The pucks 24 indicated by the arrow 62 in FIGS. 2 and 3 shows how the puck 24 has rotated from a position 61 wherein the first curved surface 26 of the puck 24 is substantially parallel to the substrate 40 in a position at which the elastic ribbons 10 are applied to the pucks 24; to an intermediate position 62; and further progression to a position 63; prior to reaching a position 64 wherein the adjacent second curved surface 28 of the puck 24 is substantially parallel to the substrate 40. The second curved surface 28 of the puck 24 in position 61 need not be perpendicular to the substrate 40, but may be in a range of approximately 45–135 degrees from parallel to the substrate 40.

Through the rotation of the rotating devices 22, the pucks 24 are radially displaced to increase the pitch from the elastic-application position 61 to the substrate bonding position 64. Meanwhile, the rotating devices 22 continue to rotate the pucks 24 toward the substrate 40. By the time the pucks 24 have been rotated to the substrate 40, the second curved surfaces 28 of the pucks 24 are in substantially parallel alignment with the substrate 40.

Figure 7:
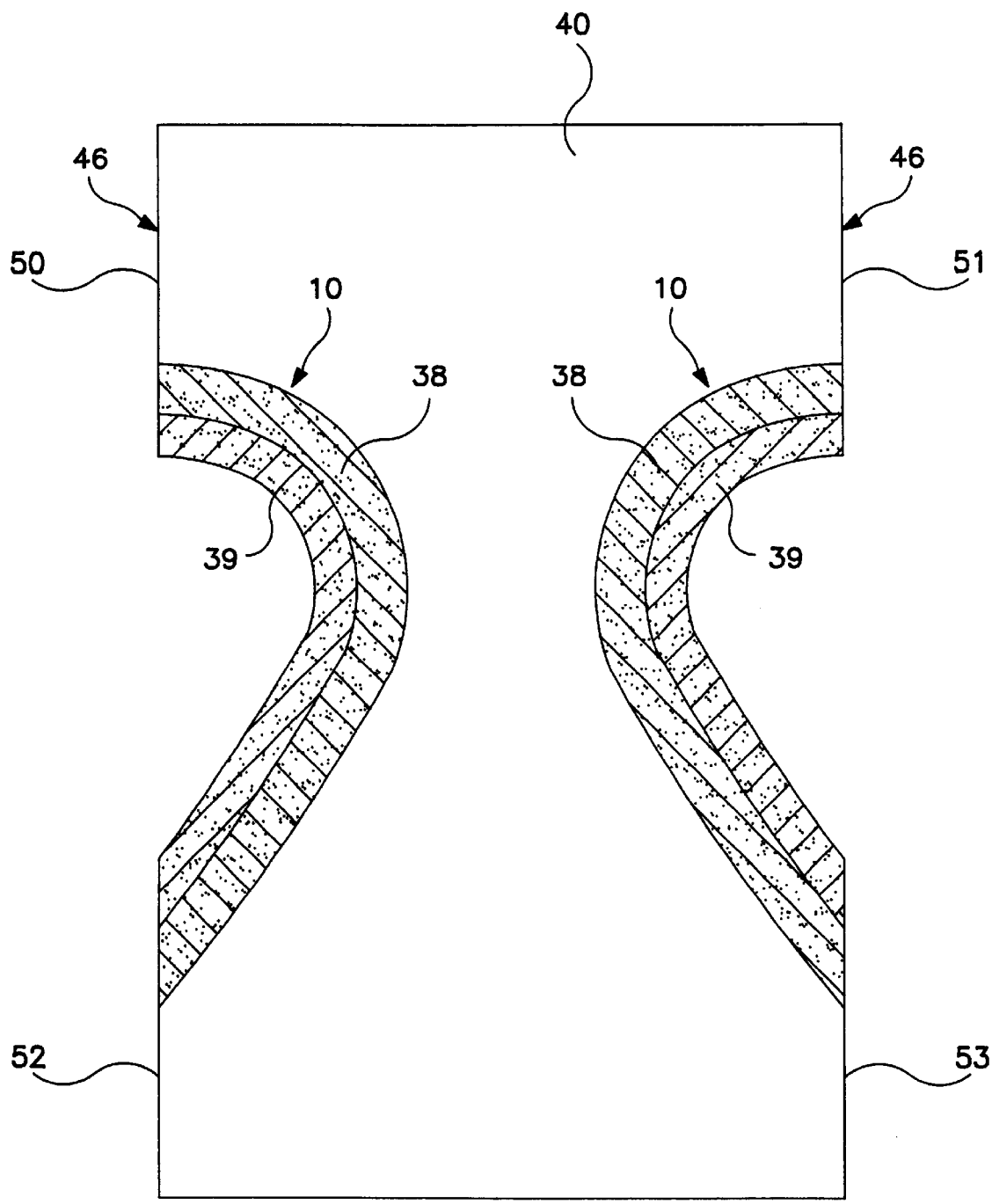
FIG. 7 is a top view of a substrate, showing a pair of curved leg elastics bonded to the substrate.

The first portions 38 of the elastic ribbons 10 are then bonded to the substrate 40 in a machine direction. The substrate 40 is typically a liner 42 or an outer cover 44 of the absorbent garment 20 (FIG. 1). As shown in FIGS. 2 and 7, the substrate 40 preferably includes corresponding curved cut-outs along parallel edges 46 of the substrate 40. The term "curved cut-out" refers to any cut-out having a curved edge, which may include a single material that is cut to form a cut-out or a plurality of materials that are bonded together to define a cut-out shape. The curved cut-outs are preferably roughly the same contour as the first curved surface 26 of the semi-curved pucks 24, but the curved cut-outs have an area slightly smaller than an area of the second curved surface 28 of each of the pucks 24. Prior to bonding the elastic ribbons 10 to the substrate 40, the curved cut-outs are aligned within a perimeter of the second curved surface 28 of the pucks 24. As a result, the second portions 39 of each of the elastic ribbons 10 are bonded to the substrate 40 along an edge adjacent each of the curved cut-outs. The first portions 38 of the elastic ribbons 10 project upward from the substrate 40 and serve as gaskets during later use of the garment 20, as explained below.

The substrate 40 can be a continuous length, as shown in FIG. 2, in which case the substrate 40 is cut into individual pieces for each garment 20 subsequent to the application of the elastic ribbons 10. Alternatively, the substrate 40 can be fed through the apparatus 3 in the form of individual pieces for each garment 20, similar to the shape of the substrate 40 in FIG. 7. The substrate 40 is preferably stretchable and/or extensible, thereby providing great flexibility, enabling the elastic ribbons 10 to be applied at low tension, and enabling a wide leg fit range.

As the elastic ribbons 10 are bonded to the substrate 40, the rotating devices 22 and the pucks 24 continue to rotate. As the rotating devices 22 advance the pucks 24 from position 64 to position 65 to position 66 (FIG. 2), the pucks 24 are returning to their initial alignment of the second curved surface 28 being substantially perpendicular to the substrate 40, or in a range of approximately 45–135 degrees from parallel to the substrate 40 as previously mentioned.

By the time the pucks 24 reach position 66 (FIG. 2), the first curved surfaces 26 are substantially parallel to the substrate 40 and in a position ready for the next elastic ribbons 10 to be guided onto the contour of the first curved surfaces 26 of the pucks 24. And so the process continues.

Each of the pucks 24 is actuated to oscillate individually using stationary spiral cam tracks and multiple cam followers positioned around a pivot point of an arm supporting each of the pucks 24. The rotating device 22 can be a high efficiency interface roll, as disclosed in U.S. Pat. No. 5,556,504. Other examples of suitable rotating devices are disclosed in U.S. Pat. Nos. 5,716,478 and 5,759,340. Additionally, cam boxes, gear racks, bevel gears, and hinge points with plows are other examples of suitable rotating devices 22.

Figure 8:
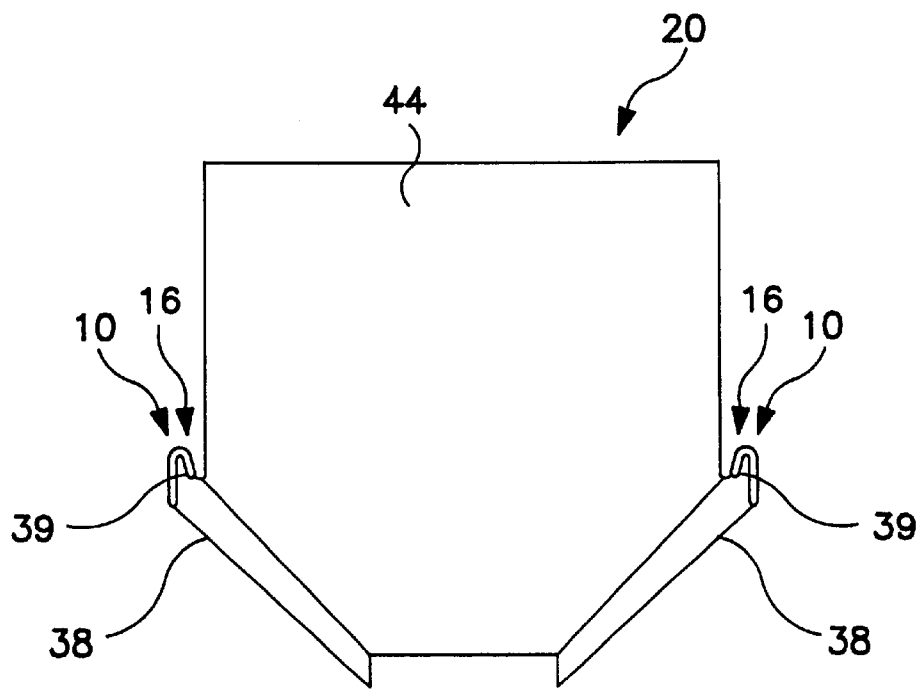
FIG. 8 is a front view of an absorbent garment showing how the leg elastics are bonded to the substrate.
Figure 9:
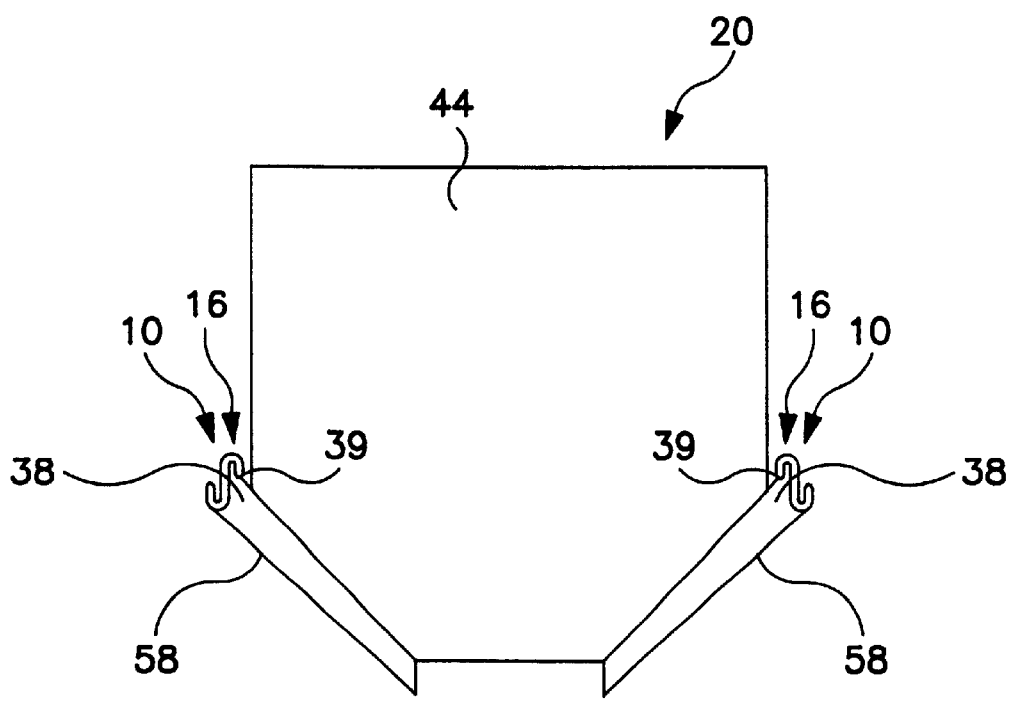
FIG. 9 is a front view of an absorbent garment showing leg elastic members with rolled edges.

FIG. 8 is a front view of an absorbent garment 20 with a pair of curved leg elastics 10 bonded to the substrate 40, in this case, the outer cover 44. FIG. 9 is a front view of an absorbent garment 20 showing the curved leg elastics 10 with rolled edges 58. The rolled edges 58 provide greater strength and reinforcement around the leg openings 12, in addition to an even more finished look. The rolled edges 58 can contain a strand of elastic to provide an even more effective gasket. A resulting seam 16 (see also FIGS. 1 and 8) joining the leg elastics 10 and the substrate 40 has a finished appearance since edges of the substrate 40 and the second portion 39 of the leg elastics 10 are both hidden from view on one side of the seam 16.

The second portions 39 of the elastic ribbons 10 can be bonded to the substrate 40 by ultrasonic bonding, as mentioned, or a variety of other techniques including adhesive bonding, thermal bonding, stitch bonding or other conventional techniques. Suitable adhesives include spray adhesives, hot melt adhesives, self-adhering elastomeric materials and the like. Each suitable bonding technique is strong enough to separate the elastic ribbons 10 from the vacuum in the pucks 24, or alternatively, from the nonslip texture of the pucks 24. As a further alternative, the vacuum itself can be released, thereby releasing the elastic ribbons 10 from the pucks 24.

Once the elastic ribbons 10 have been bonded to the substrate 40, edges 50 and 51 can be joined to edges 52 and 53, respectively, shown in FIG. 7, to form the garments 20 shown in FIGS. 1 and 8. Once the garment 20 is formed, the first portions 38 of the elastic ribbons 10 can project upward from the garment surface. During use, the first portions 38 of the elastic ribbons 10 firmly engage the wearer's skin, thereby serving as gaskets to reduce or prevent leakage through the openings of the garment 20.

The method of the invention can be used in high-speed applications, namely applications running at linear speeds of 600 feet per minute or greater. More than one semi-curved puck 24 can be located on the periphery of the rotating device 22 to enable a more expedient process. Preferably, at least three of the pucks 24 are located on the periphery of the rotating device 22. More preferably, six to eight of the pucks 24 are located on the periphery of the rotating device 22. The rotating device 22 can be adjusted to change pitch, velocity and/or machine direction spacing between application of the elastic ribbons 10 from the pucks 24 to the substrate 40.

Referring to FIG. 10, the absorbent garment 20 of FIG. 1 is shown in a partially disassembled, stretched flat state, showing a surface which faces the wearer when the garment is worn. In addition to defining the leg openings 12 and the waist opening 13 (FIG. 1), the absorbent chassis 14 also defines a pair of transversely opposed side edges 136 and a pair of longitudinally opposed waist edges, which are designated front waist edge 138 and back waist edge 139. The chassis 14 also includes a somewhat rectangular composite structure 133, a pair of transversely opposed front side panels 134, and a pair of transversely opposed back side panels 234. The composite structure 133 and side panels 134 and 234 may be integrally formed, as shown in FIG. 7, or may include two or more separate elements, as shown in FIGS. 1 and 10.

The illustrated composite structure 133 includes an outer cover 44, a body side liner 42 which is connected to the outer cover in a superposed relation, and an absorbent assembly 144 which is located between the outer cover 44 and the body side liner 42. The rectangular composite structure 133 has opposite linear end edges 145 that form portions of the front and back waist edges 138 and 139, and opposite linear, or curvilinear, side edges 147 that form portions of the side edges 136 of the absorbent chassis 14. Leg openings 12 (FIG. 1) are generally defined by portions of the transversely opposed side edges 136. For reference, arrows 48 and 49 depicting the orientation of the longitudinal axis and the transverse axis, respectively, of the training pant 20 are illustrated in FIG. 10.

The liquid permeable body side liner 42 is illustrated as overlying the outer cover 44 and absorbent assembly 144 (FIG. 10), and may but need not have the same dimensions as the outer cover 44. The body side liner 42 is desirably compliant, soft feeling, and non-irritating to the child's skin. Further, the body side liner 42 can be less hydrophilic than the absorbent assembly 144, to present a relatively dry surface to the wearer and permit liquid to readily penetrate through its thickness.

The absorbent assembly 144 (FIG. 10) is positioned between the outer cover 44 and the body side liner 42, which components can be joined together by any suitable means, such as adhesives, as is well known in the art. The absorbent assembly 144 can be any structure which is generally compressible, conformable, non-irritating to the child's skin, and capable of absorbing and retaining liquids and certain body wastes. The absorbent assembly 144 can be manufactured in a wide variety of sizes and shapes, and from a wide variety of liquid absorbent materials commonly used in the art. For example, the absorbent assembly 144 can suitably include a matrix of hydrophilic fibers, such as a web of cellulosic fluff, mixed with particles of a high-absorbency material commonly known as superabsorbent material. In a particular embodiment, the absorbent assembly 144 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsbrbent particles can be substantially homogeneously mixed with the hydrophilic fibers or can be nonuniformly mixed. The fluff and superabsorbent particles can also be selectively placed into desired zones of the absorbent assembly 144 to better contain and absorb body exudates. The concentration of the superabsorbent particles can also vary through the thickness of the absorbent assembly 144. Alternatively, the absorbent assembly 144 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Michigan, U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 144 is generally rectangular in shape, and includes a blend of wood pulp fluff and superabsorbent material. One preferred type of fluff is identified with the trade designation CR1654, available from Kimberly-Clark Corporation, Neenah, Wis., U.S.A., and is a bleached, highly absorbent sulfate wood pulp containing primarily soft wood fibers. As a general rule, the superabsorbent material is present in the absorbent assembly 144 in an amount of from about 0 to about 90 weight percent based on total weight of the absorbent assembly. The absorbent assembly 144 suitably has a density within the range of about 0.10 to about 0.35 grams per cubic centimeter. The absorbent assembly 144 may or may not be wrapped or encompassed by a suitable tissue wrap that maintains the integrity and/or shape of the absorbent assembly.

The absorbent chassis 14 can also incorporate other materials that are designed primarily to receive, temporarily store, and/or transport liquid along the mutually facing surface with the absorbent assembly 144, thereby maximizing the absorbent capacity of the absorbent assembly. One suitable material is referred to as a surge layer (not shown) and includes a material having a basis weight of about 50 grams per square meter, and including a through-air-bonded-carded web of a homogenous blend of 60 percent 3 denier bicomponent fiber including a polyester core/polyethylene sheath, commercially available from BASF Corporation, and 40 percent 6 denier polyester fiber, commercially available from Hoechst Celanese Corporation, in Portsmouth, Virginia, U.S.A.

A wide variety of elastic materials may be used for the leg elastics 10. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastics 10 include a plurality of dry-spun coalesced multifilament spandex elastomeric threads sold under the trade name LYCRA® and available from E.I. DuPont de Nemours and Company, Wilmington, Delaware, U.S.A.

Each of the leg elastics 10 preferably has a width of about 0.5 inch (1.27 cm) to about 5 inches (12.7 cm), more preferably about 1 inch (2.54 cm) to about 4 inches (10.16 cm), most preferably about 1.5 inches (3.81 cm) to about 2.5 inches (6.35 cm). Second portions 39 of the leg elastics 10 preferably have a width of about 0.25 inch (0.635 cm) to about 4 inches (10.16 cm), more preferably about 0.5 inch (1.27 cm) to about 3 inches (7.62 cm), most preferably about 1 inch (2.54 cm) to about 2 inches (5.08 cm). The length of the leg elastics 10 once cut by the cutting device 34 should substantially cover a circumference of the leg opening 12. Depending on the garment size, the leg elastics 10 may have a length of at least about 4 inches, preferably at least about 8 inches, more preferably at least about 12 inches. Of course, the lengths are shorter if the leg elastics 10 are not intended to fully encircle a wearer's legs. Furthermore, each of the leg elastics 10 preferably has elongation of 25–350%, more preferably about 30–260%, most preferably about 35–200%.

The substrate 40 is preferably the outer cover 44 and desirably includes a material that is substantially liquid impermeable, and can be elastic, stretchable or nonstretchable. The outer cover 44 can be a single layer of liquid impermeable material, but desirably includes a multi-layered laminate structure in which at least one of the layers is liquid impermeable. For instance, the outer cover 44 can include a liquid permeable outer layer and a liquid impermeable inner layer that are suitably joined together, such as by a laminate adhesive (not shown). Suitable laminate adhesives, which can be applied continuously or intermittently as beads, a spray, parallel swirls, or the like, can be obtained from Findley Adhesives, Inc., of Wauwatosa, Wisconsin, U.S.A., or from National Starch and Chemical Company, Bridgewater, New Jersey, U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively clothlike texture to the wearer.

The inner layer of the outer cover 44 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 44 when a single layer, prevents waste material from wetting articles, such as bed-sheets and clothing, as well as the wearer and caregiver. A suitable liquid impermeable film for use as a liquid impermeable inner layer, or a single layer liquid impermeable outer cover 44, is a 0.02 millimeter polyethylene film commercially available from Huntsman Packaging of Newport News, Virginia, U.S.A. If the outer cover 44 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 44. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minnesota.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 44 and bodyside liner 42 can include elastomeric materials, it can be desirable in some embodiments for the composite structure to be generally inelastic, where the outer cover, the bodyside liner and the absorbent assembly include materials that are generally not elastomeric.

As noted previously, the illustrated training pant 20 can have front and back side panels 134 and 234 disposed on each side of the absorbent chassis 14 (FIGS. 1 and 10). These transversely opposed front side panels 134 and transversely opposed back side panels 234 can be permanently bonded to the composite structure 133 of the absorbent chassis 14 and are releasably attached to one another by a fastening system 80 (FIG. 1). More particularly, as shown best in FIG. 10, the front side panels 134 can be permanently bonded to and extend transversely beyond the linear side edges 147 of the composite structure 133 along attachment lines 69, and the back side panels 234 can be permanently bonded to and extend transversely beyond the linear side edges of the composite structure along attachment lines 69. The side panels 134 and 234 may be attached using attachment means known to those skilled in the art such as adhesive, thermal or ultrasonic bonding. The side panels 134 and 234 can also be formed as a portion of a component of the composite structure 133, such as the outer cover 44 or the body side liner 42.

Each of the side panels 134 and 234 can include one or more individual, distinct pieces of material. In particular embodiments, for example, each side panel 134 and 234 can include first and second side panel portions that are joined at a seam, with at least one of the portions including an elastomeric material (not shown). Still alternatively, each individual side panel 134 and 234 can include a single piece of material which is folded over upon itself along an intermediate fold line (not shown).

The side panels 134 and 234 desirably include an elastic material capable of stretching in a direction generally parallel to the transverse axis 49 of the training pant 20. In particular embodiments, the front and back side panels 134 and 234 may each include an interior portion 78 disposed between a distal edge 68 and a respective front or back center panel 135 or 235. In the illustrated embodiment in FIG. 10, the interior portions 78 are disposed between the distal edges 68 and the side edges 147 of the rectangular composite structure 133. The elastic material of the side panels 134 can be disposed in the interior portions 78 to render the side panels elastomeric in a direction generally parallel to the transverse axis 49. Most desirably, each side panel 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 69 to the distal edge 68 and a width of about 2 centimeters, are all elastomeric.

Suitable elastic materials, as well as one described process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material includes a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 44 or body side liner 42, or stretchable but inelastic materials.

The absorbent chassis 14 and the fastening system 80 together define a refastenable pant having a waist opening 13 and a pair of leg openings 12 (FIG. 1). When the fastening system is engaged, it can be appreciated that the refastenable pant includes a pair of elastomeric front side panels 134 extending from the waist opening to each leg opening, a pair of elastomeric back side panels 234 extending from the waist opening to each leg opening, a pair of refastenable seams 88 (FIG. 1) extending from the waist opening to each leg opening and positioned between the elastomeric front and back side panels, an elastomeric front waistband 154 positioned between the pair of elastomeric front side panels 134, an elastomeric back waistband 156 positioned between the pair of elastomeric back side panels 234, and a pair of curved leg elastics 10 which encircle each leg opening 12.

As described herein, the various components of the training pant 20 can be integrally assembled together employing various types of suitable attachment means, such as adhesive, sonic and thermal bonds or combinations thereof. The resulting product is an absorbent garment 20 having a comfortable, gasket-like fit and an aesthetically pleasing, finished look about the leg openings 12. The gasket-like fit can eliminate a need for separately attached side flaps, thereby eliminating additional time and material costs. The pant-like absorbent garment 20 can be sized and tailored for a wide variety of uses including, for example, diapers, training pants, swimwear, adult incontinence garments, and the like. The curved leg elastics of the present invention can also be used for curved standing leg cuffs. Alternatively, leak guard flaps can be attached to an absorbent garment in the same manner as the leg elastics are attached to an absorbent garment in the present invention.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of producing curved leg elastics comprising the steps of:
    guiding a pair of elastic ribbons onto a pair of complementary pucks, each puck having a first curved surface;
    directing each elastic ribbon to follow a contour of the first curved surface of one of the pucks;
    severing each of the elastic ribbons into a discrete piece;
    moving the pucks toward a substrate; and
    bonding the pieces of the elastic ribbons to the substrate.

2. The method of claim 1, wherein the step of moving the pucks comprises rotating the pucks toward the substrate.

3. The method of claim 2, wherein the pucks are oscillated by about 90 degrees from a plane substantially perpendicular to the substrate.

4. The method of claim 1, wherein the step of moving the pucks comprises rotating the pucks in a plane substantially parallel to the substrate.

5. The method of claim 4, wherein the step of moving the pucks further comprises oscillating the pucks from a plane substantially perpendicular to the substrate.

6. The method of claim 1 wherein the pucks are attached to a rotating device.

7. The method of claim 6, further comprising the step of adjusting the rotating device to change machine direction spacing of the pucks.

8. The method of claim 1, wherein each of the pucks further comprises a second curved surface adjacent the first curved surface.

9. The method of claim 8 wherein the first curved surfaces of the pucks each at least partially comprise a nonslip texture.

10. The method of claim 8, further comprising the step of directing a portion of each elastic ribbon onto the second curved surface of one of the pucks as the elastic ribbon is directed to follow the contour of the first curved side of the puck.

11. The method of claim 10, wherein the portion of each of the pieces of the elastic ribbons on the second curved surface of the puck is bonded to the substrate.

12. The method of claim 1, further comprising the step of applying a vacuum to hold the elastic ribbons onto the pucks.

13. The method of claim 1, wherein the bonding step comprises applying an adhesive to at least one of the elastic ribbons and the substrate.

14. The method of claim 1 wherein the bonding step comprises ultrasonically bonding the pieces of elastic ribbon to the substrate.

15. The method of claim 1 wherein the substrate comprises a stretchable material.

16. The method of claim 1 wherein the substrate comprises curved cut-outs along two parallel edges.

17. A method of attaching leg elastics to a substrate comprising the steps of:
    guiding a pair of elastic ribbons onto a pair of opposing pucks, each puck having a first curved surface and a second surface adjacent the first curved surface;
    stretching and displacing each of the elastic ribbons so that the elastic ribbons each follow a contour of the curved surface of one of the pucks and a portion of each elastic ribbon is folded onto the second surface of the puck;
    severing each of the elastic ribbons into a discrete piece;
    rotating the pucks toward the substrate; and
    bonding the second surface portion of each of the pieces of the elastic ribbons to a curved edge of the substrate.

18. The method of claim 17 wherein the pucks are attached to a rotating device.

19. The method of claim 17, wherein the pucks are rotated in a plane that is substantially parallel to the substrate.

20. The method of claim 17, wherein the pucks are oscillated from a plane that is substantially perpendicular to the substrate.

21. The method of claim 17 wherein the pair of pucks is aligned during bonding such that the first curved surfaces of the pucks face each other.

22. The method of claim 17, further comprising the step of applying a vacuum to hold the elastic ribbons on the pucks.

23. The method of claim 17 wherein the first curved surfaces of the pucks each at least partially comprise a nonslip texture.

24. The method of claim 17, farther comprising the step of applying an adhesive to at least one of the elastic ribbons and the substrate, to bond the second surface portion of each of the elastic ribbons to the substrate.

25. The method of claim 17 wherein the bonding step comprises ultrasonically bonding the pieces of elastic ribbon to the substrate.

26. The method of claim 17 wherein the substrate comprises a stretchable material.

27. A method of attaching leg elastics to a substrate comprising the steps of:
    guiding a pair of continuous elastic ribbons onto a pair of pucks;
    placing each elastic ribbon so that the elastic ribbon follows a contour of a first curved surface of one of the pucks and a portion of the elastic ribbon is folded over an edge of the puck onto a second surface of the puck;
    severing the elastic ribbons into discrete pieces;
    rotating the pucks toward the substrate; and
    bonding the second surface portion of each piece of the elastic ribbon to the substrate.

28. The method of claim 27, wherein the pucks are oscillated by about 45 to about 135 degrees in a plane substantially perpendicular to the substrate.

29. The method of claim 27 wherein each of the pucks is attached to a rotating device which rotates in a direction substantially parallel to the substrate.

* * * * *